United States Patent [19]

Cassandrini et al.

[11] 4,086,204

[45] Apr. 25, 1978

[54] NOVEL POLYTRIAZINE COMPOUNDS

[75] Inventors: Paolo Cassandrini, Bologna; Antonio Tozzi, Sasso Marconi, both of Italy

[73] Assignee: Chimosa Chimica Organica S.p.A., Marconi, Italy

[21] Appl. No.: 699,162

[22] Filed: Jun. 23, 1976

[30] Foreign Application Priority Data

Dec. 4, 1975 Italy ................ 52527 A/75

[51] Int. Cl.$^2$ .............. C08K 5/00; C07D 251/00; C07D 251/54; C07D 239/00

[52] U.S. Cl. .............. 260/45.8 NT; 260/2 R; 260/61; 260/79; 544/182; 544/196; 544/207

[58] Field of Search ......... 260/45.8 NT, 248 CS, 260/249.8, 249.6, 79, 61, 2 R

[56] References Cited

U.S. PATENT DOCUMENTS

| | | | |
|---|---|---|---|
| 2,640,047 | 5/1953 | Thurston | 260/79 |
| 3,155,628 | 11/1964 | Bloomfield | 260/2 R |
| 3,297,639 | 1/1967 | Picklesimer et al. | 260/2 R |
| 3,301,797 | 1/1967 | Drucker et al. | 260/2 R |
| 3,530,121 | 9/1970 | Heimberger et al. | 260/249.8 |
| 3,576,805 | 4/1971 | Cantrall et al. | 260/249.6 |
| 3,850,918 | 11/1974 | Muller et al. | 260/45.8 NT |
| 3,894,991 | 7/1975 | Neuray et al. | 260/79 |
| 3,925,376 | 12/1975 | Chalmers et al. | 260/248 CS |
| 3,978,028 | 8/1976 | Sundermann et al. | 260/61 |

FOREIGN PATENT DOCUMENTS

| | | |
|---|---|---|
| 651,967 | 12/1964 | Belgium. |
| 276,038 | 10/1964 | Netherlands. |

*Primary Examiner*—V. P. Hoke
*Attorney, Agent, or Firm*—Cushman, Darby & Cushman

[57] ABSTRACT

Novel tetraalkyl piperidine radical containing polytriazine compounds are produced by reacting a dihalogentriazine with a bifunctional compound containing amine, alcohol, mercaptan or phenol groups at least one of the bifunctional compounds containing a tetraalkyl piperidine radical. The compounds are valuable light stabilizers for synthetic polymers, particularly polyolefin in the form of fibers or films.

28 Claims, No Drawings

NOVEL POLYTRIAZINE COMPOUNDS

BACKGROUND OF THE INVENTION

1. Field of the Invention

The present invention relates to novel polytriazine compounds which are useful for improving the stability to light, heat and oxidation of polymeric substances.

2. Description of the Prior Art

It is known that synthetic polymers are liable to undergo a severe deterioration of their physical and chemical properties when they are exposed to sunlight or other ultraviolet light source.

In order to improve the stability to light of said synthetic polymers, various stabilizers have been proposed, some of which have found a wide commercial acceptance in the field, such as some benzophenones, benzotriazoles, aromatic salicylates, α-cyanoacrylic acid esters, organo-tin compounds and the like, which, although having a certain efficiency level, are not successful to solve the problem completely, so that a need of more efficient stabilizers is very much felt in this field.

SUMMARY

An object of the invention is to provide new compounds consisting of triazine polymers having the following general formula:

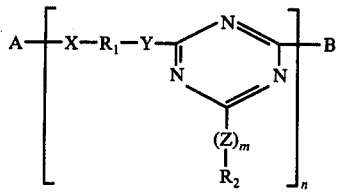

in which:

X, Y, Z the same or different, represent —O—, —S—,

with $R_3$ being hydrogen, a straight or branched chain alkyl having 1 to 18 C atoms, a cycloalkyl having 5 to 18 C atoms, a substituted or non-substituted aryl having 6 to 18 C atoms, an aralkyl having 7 to 18 C atoms, or $R_3$ represents a piperadine radical of the formula:

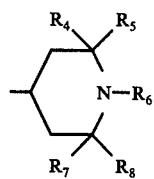

wherein each of $R_4$, $R_5$, $R_7$ and $R_8$ the same or different, are a $C_1$ to $C_6$ alkyl, and $R_6$ is hydrogen, O, a $C_1$ to $C_{18}$ straight or branched chain alkyl, a $C_2$ to $C_{18}$ alkenyl or alkynyl, or a $C_7$ to $C_{18}$ aralkyl;

$R_1$ is a $C_2$ to $C_{18}$ straight or branched chain alkylene, a $C_5$ to $C_{18}$ cycloalkylene, a $C_6$ to $C_{18}$ arylene, and a $C_7$ to $C_{18}$ aralkylene.

Furthermore, —X—$R_1$—Y— camn be a bivalent radical of a heterocycle compound with 6 to 8 members having 2 nitrogen atoms; in such case X and Y are a disubstituted nitrogen atom respectively;

—X—$R_1$—Y— can be also replaced by the radical

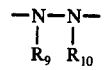

in which $R_9$, $R_{10}$ the same or different, are H, a $C_1$ to $C_{12}$ alkyl, a $C_5$ to $C_{12}$ cycloalkyl, a $C_6$ to $C_{12}$ aryl, a $C_7$ to $C_{12}$ aralkyl;

m is either 0 to 1;

$R_2$ represents —H, —Cl, —Br, —OH, a straight or branched chain $C_1$ to $C_{18}$ alkyl, a $C_5$ to $C_{18}$ cycloalkyl, a substituted or not substituted $C_6$ to $C_{18}$ aryl, a $C_7$ to $C_{18}$ aralkyl, a piperidine radical of formula (II), or $R_2$ represents the radical

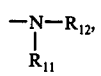

in which $R_{11}$, $R_{12}$ are hydrogen, $C_1$ to $C_{12}$ alkyl, $C_5$ to $C_{12}$ cycloalkyl, $C_6$ to $C_{12}$ aryl, or $C_7$ to $C_{12}$ aralkyl;

when m is 1, the radical $R_2$—Z— can be the same as —X—$R_1$—YH, where X, Y, $R_1$ have the meaning above indicated.

n is an integer from 2 to 200;

A and B represent the terminal groups. By the term "terminal groups" it is meant the terminal groups of a molecule of formula (I) resulting from the polymerization reaction, which generally are a residue of functional groups. The nature of said residue depends on the reaction conditions, the nature and amount of the reactants used in the reaction, for example, as it is known to one skilled in the art. Said residue is preferably H for A and —X—$R_1$—YH for B, in that it is preferred using an excess of bifunctional compound in the reaction for controlling the molecular weight, as will be more fully described later.

In formula (I) there is the condition that either radical —X—$R_1$—Y— or —(Z)$_m$—$R_2$, or both contain at least one piperidine radical of formula (II).

An additional object of the invention is to provide a method for the preparation of the above compounds of formula (I).

A further object of the invention is to provide new stabilizers for synthetic polymers for improving their stability to light, heat and oxidation.

A further object of the invention is to provide a composition of material comprising a synthetic polymer and an amount of a stabilizer of formula (I) effective to improve the weather resistance thereof, as well as additional optional additives.

THE DETAILED DESCRIPTION

In accordance with this invention, in a triazine polymer of formula (I), the following preferred embodiments are intended for the various substituent groups: $R_3$ represents hydrogen, methyl, ethyl, n-butyl, isobutyl, n-octyl, 2-ethylhexyl, n-dodecyl, n-octadecyl, cyclohexyl, 3,3,5-trimethylcyclohexyl, phenyl, o-, m-, p-toluyl, α- or β-naphthyl, benzyl, p-methylbenzyl, 2,2,6,6-tetramethyl-4-piperidyl, 1,2,2,6,6-pentamethyl-4-piperidyl, 1-ethyl-2,2,6,6-tetramethyl-4-piperidyl, 1-propyl-2,2,6,6-tetramethyl-4-piperidyl.

Representatives of $R_1$ are ethylene, 1,2-propylene, trimethylene, hexamethylene, 2,2,4-trimethylhexamethylene, 2,4,4-trimethylhexamethylene, decamethylene, 1,4-cyclohexylene, 4,4'-methylenedicyclohexylene, o-, m-, p-phenylene, o-, m-, p-xylylene.

The radical —X—$R_1$—Y— can be

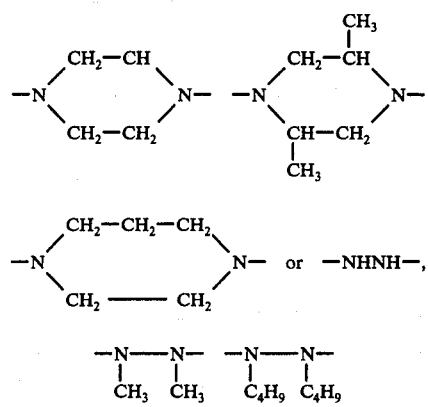

Additionally to hydrogen, chlorine, bromine, —OH, representatives of $R_2$, are —$NH_2$,—$N(CH_3)_2$, methyl, ethyl, isopropyl, n-butyl, isobutyl, n-octyl, 1,1,3,3-tetramethylbutyl, n-dodecyl, n-octadecyl, cyclohexyl, 3,3,5-trimethylcyclohexyl, phenyl, 2,6-dimethylphenyl, o-, m-, p-toluyl, α-, or β-naphthyl, benzyl, p-methylbenzyl, 2,2,6,6-tetramethyl-4-piperidyl, 1,2,2,6,6-pentamethyl-4-piperidyl, 1-ethyl-2,2,6,6-tetramethyl-4-piperidyl, 6-(2,2,6,6-tetramethyl-4-piperidylamino)-hexyl, 2-(2,2,6,6-tetramethyl-4-piperidylamino)-ethyl.

PREPARATION

The polytriazines of the present invention can be prepared by various procedures. A first procedure is reacting a 2,4-dihalogen-1,3,5-triazine of formula (III).

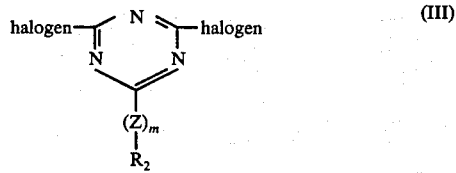

(III)

in which halogen is preferably chlorine, with a bifunctional compound (IV)

HX—$R_1$—Y—H     (IV)

When in formula (I), m is one, dihalogentriazines of formula (III) can be prepared by reacting a cyanuric halide, preferably chloride, with 1 mole of a compound of formula (V)

$R_2$—Z—H     (V)

An alternative procedure is reacting a cyanuric halide with a bifunctional compound of formula (IV); depending on the mole ratios used it is possible to obtain compounds according to either formula (VI)

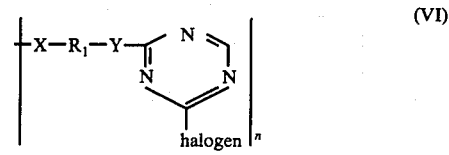

or formula (VII)

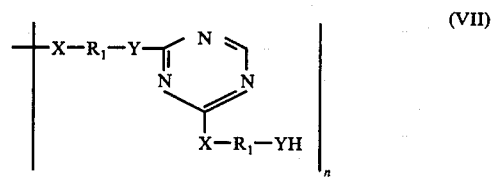

The polytriazines of formula (VI) can be successively reacted with a compound of formula (V).

The reaction of the halogentriazines with the compounds of formula (IV) or compounds of formula (V) is carried out in the presence of an inert solvent such as acetone, dioxane, toluene, xylene, in a temperature range from −10° C and the solvent boiling temperature. The reaction is carried out in the presence of organic or inorganic bases for fixing hydrogen halide. Preferred examples of base useful to said purpose are triethylamine or tributylamine, sodium hydroxide, carbonate or bicarbonate, potassium hydroxide or carbonate, sodium alcoholates in the case that the compounds of formula (IV) or (V) are alcohols or glycols, sodium mercaptides in the case that the reactants of formula (IV) or (V) are mono- or di-mercaptans; it is further possible to use an amine excess, when reacting a compound of formula (VI) with a compound of formula (V), in which Z is

The mole ratio of compounds (III) to compounds (IV) can range from 1:1.5 to 1.5:1, preferably from 1:1 to 1:1.2.

When reacting a cyanuric halide with a compound (IV) to obtain products of formula (VI), the mole ratio between said compounds is preferably in a range from 1:1 to 1:1.2.

When reacting a cyanuric halide with a compound (IV) to obtain products of formula (VII), the mole ratio between said compounds is in a range from 1:2.5 to 1:2, more preferably from 1:2.4 to 1:2.1.

Particular examples of dihaloen triazines (III) which can be employed to obtain products of formula (I), are:

2,4-dichloro-1,3,5-triazine,
2,4-dichloro-6-methyl-1,3,5-triazine,
2,4-dichloro-6-ethyl-1,3,5-triazine,
2,4-dichloro-6-phenyl-1,3,5-triazine,
2,4-dichloro-Lb 6-n-butoxy-1,3,5-triazine,
2,4-dichloro-6-n-octyloxy-1,3,5-triazine,
2,4-dichloro-6-cyclohexyloxy-1,3,5-triazine,
2,4-dichloro-6-phenoxy-1,3,5-triazine,
2,4-dichloro-6(2,6-dimethylphenoxy)1,3,5-triazine,
2,4-dichloro-6-benzyloxy-1,3,5-triazine,
2,4-dichloro-6-(2,2,6,6-tetramethyl-4-piperidyloxy) 1,3,5-triazine,
2,4-dichloro-6-n-octylthio-1,3,5-triazine, 2,4-dichloro-6-amino-1,3,5-triazine,
2,4-dichloro-6-n-butylamino-1,3,5-triazine,
2,4-dichloro-6-n-octylamino-1,3,5-triazine,
2,4-dichloro-6-cyclohexylamino-1,3,5-triazine,
2,4-dichloro-6-phenylamino-1,3,5-triazine,
2,4-dichloro-6-diethylamino-1,3,5-triazine,
2,4-dichloro-6-(2,2,6,6-tetramethyl-4-piperidylamino)-1,3,5-triazine,
2,4-dichloro-6[N(2,2,6,6-tetramethyl-4-piperidyl)-n-butylamino]1,3,5-triazine,
2,4-dichloro-6[N(2,2,6,6-tetramethyl-4-piperidyl)-n-octylamine]1,3,5-triazine, Representatives of compounds of formula (IV) are:

hydrazine,
1,2-dimethylhydrazine,
ethyleneglycol,
1,3-dihydroxypropane,
1,6-dihydroxyhexane,
resorcinol,
2,2-bis (4-hydroxyphenyl) propane,
bis (3,5-dimethyl-4-hydroxyphenyl)-methane,
1,4-bis-(hydroxymethyl)-cyclohexane,
1,2-dimercaptoethane,
2-hydroxyethylamine,
2-mercaptoethylamine,
1,2-diaminoethane,
1,3-diaminopropane,
1,6-diaminohexane
1,4-diaminocyclohexane,
1,4-bis (aminomethyl) cyclohexane,
p-phenylenediamine,
4,4'-diaminodiphenylmethane,
p-xylylenediamine,
m-xylylenediamine,
1,2-bis-(n-butylamino)-ethane,
1,6-bis-(ethylamino)-hexane,
piperazine,
2,5-dimethylpiperazine, homopiperazine,
1,2-bis-(2,2,6,6-tetramethyl-4-piperidylamino)-ethane,
1,3-bis-(2,2,6,6-tetramethyl-4-piperidylamino)-propane,
1,6-bis-(2,2,6,6-tetramethyl-4-piperidylamino)-hexane, Representatives of compounds of formula (V) are:
methyl-, ethyl-, n-butyl, n-octyl-, 2-ethylhexyl-, n-dodecyl-, cyclohexyl-, benzyl-alcohol; 2,2,6,6-tetramethyl-4-piperidinol, phenol, 2,6-dimethylphenol, n-butylmercaptan, n-octylmercaptan, ethylamine, n-butylamine, n-octylamine, 1,1,3,3-tetramethylbutylamine, cyclohexylamine, 3,3,5-trimethylcyclohexylamine, aniline, p-toluidine, benzylamine, diethylamine, di-n-butylamine, 2,2,6,6-tetramethyl-4-piperidylamine, 1,2,2,6,6-pentamethyl-4-piperidylamine, 2,2,6,6-tetramethyl-4-n-butylaminopiperidine, 2,2,6,6-tetramethyl-4-n-octylaminopiperidine, hydrazine, 1,1-dimethylhydrazine, hydroxylamine.

In order to further illustrate the present invention, some examples of preparation are given in the following for an illustrative and not limitative purpose.

EXAMPLE 1

22.1 g (0.1 moles) of 2,4-dichloro-6-n-butylamino-1,3,5-triazine, 43.34 g (0.11 moles) of 1,6-bis (2,2,6,6-tetramethyl-4-piperidylamino) hexane, 8 g (0.2 moles) of NaOH and 300 ml of toluene were refluxed for 16 hours.

After filtering to remove sodium chloride and evaporating the solvent, a light colored resinous substance of reduced viscosity (1% in chloroform at 25° C) = 0.10 was obtained.

EXAMPLE 2

(a) 2,4-dichloro-6[N(2,2,6,6-tetramethyl-4-piperidyl)-n-butylamino]-1,3,5-triazine was primarily prepared as a starting compound for producing a polytriazine according to the invention.

A solution of 18.4 g (0.1 moles) of cyanuric chloride in 180 ml of acetone was additioned at 0° C with 21.2 g (0.1 moles) of 2,2,6,6-tetramethyl-4-n-butylaminopiperidine dissolved in 100 ml of acetone and 4 g of sodium hydroxide dissolved in 40 ml of water.

The precipitate so obtained was filtered after 6 hours at 0° C. After drying a solid product was obtained, which was purified by distillation: b.p. 151°–2°/0.1, m.p. 56°–58° C. Cl% 19,65 (calculated for $C_{16}H_{27}Cl_2N_5$: 19,72%).

(b) 36 g (0.1 moles) of 2,4-dichloro-6[N(2,2,6,6-tetramethyl-4-piperidyl)-n-butylamino]1,3,5-triazine as prepared in example 2 a), 12.7 g (0.11 moles) of hexamethylenediamine, 8 g of sodium hydroxide and 200 ml of toluene were refluxed for 16 hours.

After filtering to remove sodium chloride and evaporating the reaction solvent a light colored resinous substance of reduced viscosity (1% in chloroform at 25° C) 0.12 was obtained.

EXAMPLE 3

18.4 g (0.1 moles) of cyanuric chloride, 39.4 g (0.1 moles) of 1,6-bis(2,2,6,6-tetramethyl)-4-piperidylamino) hexane, 8 g of sodium hydroxide and 250 ml of toluene were heated 8 hours at 40° C.

The mixture was additioned with 26.8 g (0.1 moles) of 2,2,6,6-tetramethyl-4-n-octylamino-piperidine and 4 g of sodium hydroxide and refluxed for 16 hours.

After filtering to remove sodium chloride and evaporating the reaction solvent a resinous substance of reduced viscosity (1% in chloroform at 25° C) = 0.13 was obtained.

EXAMPLE 4

(a) 2,4-dichloro-6-(2,6-dimethylphenoxy)1,3,5-triazine, was primarily prepared as a starting compound for producing a polytriazine according to the invention.

A solution of 18.4 g (0.1 moles) of cyanuric chloride in 200 ml of acetone was additioned at 0° C with a solution of 12.2 g (0.1 moles) of 2,6-dimethylphenol, 4 g of sodium hydroxide (0.1 moles) and 100 ml of water. The precipitate so obtained was filtered at 0° C 6 hours after.

After drying and crystallizing from hexane, a white powder was obtained melting at 114°–115° C, Cl% 26.18 (calculated for $C_{11}H_9Cl_2N_3O$: 26.29%).

(b) 27 g (0.1 moles) of 2,4-dichloro-6-(2,6-dimethylphenoxy)1,3,5-triazine as prepared in example 4 a), 33.8 g (0.1 moles) of 1,2-bis (2,2,6,6-tetramethyl-4-piperidylamino)-ethane, 8 g of sodium hydroxide and 250 ml of toluene were refluxed for 16 hours.

After filtering to remove sodium chloride and evaporating the reaction solvent a resinous substance of reduced viscosity (1% in chloroform at 25° C) = 0.14 was obtained.

EXAMPLE 5

29.4 g (0.1 moles) of 2,4-dichloro-6-n-octylthio-1,3,5-triazine, 33.8 g (0.1 moles) of 1,2-bis-(2,2,6,6-tetramethyl-4-piperidylamino)-ethane, 8 g of sodium hydroxide and 250 ml of toluene were refluxed for 16 hours.

After filtering to remove sodium chloride and evaporating the reaction solvent, a resinous substance of reduced viscosity (1% in chloroform at 25° C) = 0.17 was obtained.

EXAMPLE 6

35.4 g (0.09 moles) of 1,6-bis-(2,2,6,6-tetramethyl-4-piperidylamino)-hexane, 7.36 g (0.04 moles) of cyanuric chloride, 4.8 g of sodium hydroxide and 250 ml of toluene were fluxed for 16 hours.

After filtering to remove sodium hydroxide and evaporating the reaction solvent, a solid substance of reduced viscosity (1% in chloroform at 25° C) = 0.10 was obtained.

EXAMPLE 7

36 g (0.1 moles) of 2,4-dichloro-6[N(2,2,6,6-tetramethyl-4-piperidyl)-n-butylamino]1,3,5-triazine as prepared in example 2 a) dissolved in 200 ml of acetone were additioned with 100 ml of water, containing in solution 12.1 g (0.11 moles) of resorcinol and 8 g of sodium hydroxide and refluxed for 16 hours.

Acetone was removed, the precipitate was filtered, washed with water and dried.

A solid product of reduced viscosity (1% in chloroform at 25° C) = 0.10 was obtained.

EXAMPLE 8

A solution of 18.4 g (0.1 moles) of cyanuric chloride in 200 ml of toluene was additioned at 10° C with a solution of 39.4 (0.1 moles) of 1,6-bis (2,2,6,6-tetramethyl-4-piperidylamino) hexane in 100 ml of toluene and 8 g of sodium hydroxide.

The mixture was warmed at 40° C under stirring for 12 hours.

After filtering to remove sodium chloride and evaporating the reaction solvent, a solid substance of reduced viscosity (1% in chloroform at 25° C) = 0.16 was obtained.

The products as obtained in the preparation examples are summarized in the following table 1, in which the respective substituent groups are listed according to the definition of the previously specified formula (I).

Table 1

| Example No. | X | $R_1$ | Y | Z | $R_2$ | m |
|---|---|---|---|---|---|---|
| 1 | >N—[piperidyl]—NH | —(CH$_2$)$_6$— | >N—[piperidyl]—NH | NH | n-butyl | 1 |
| 2 | NH | —(CH$_2$)$_6$— | NH | >N—[piperidyl]—NH | n-butyl | 1 |
| 3 | >N—[piperidyl]—NH | —(CH$_2$)$_6$— | >N—[piperidyl]—NH | >N—[piperidyl]—NH | n-octyl | 1 |
| 4 | >N—[piperidyl]—NH | —(CH$_2$)$_2$— | >N—[piperidyl]—NH | —O— | 2,6-dimethylphenyl | 1 |
| 5 | >N—[piperidyl]—NH | —(CH$_2$)$_2$— | >N—[piperidyl]—NH | —S— | n-octyl | 1 |
| 6 | >N—[piperidyl]—NH | —(CH$_2$)$_6$— | >N—[piperidyl]—NH | >N—[piperidyl]—NH | —(CH$_2$)$_6$—NH—[piperidyl-NH] | 1 |

Table 1-continued

| Example No. | X | R₁ | Y | Z | R₂ | m |
|---|---|---|---|---|---|---|
| 7 | O | m-pheny-lene | O | 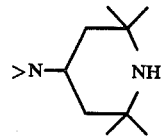 | n-butyl | 1 |
| 8 | 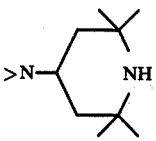 | —(CH₂)₆— | 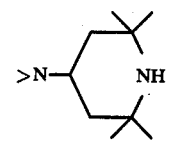 | — | Cl | 0 |

LIGHT STABILIZATION TESTS

The polytriazine compounds of formula (I) are useful and valuable agents for improving the stability to light, heat and oxidation of synthetic polymers such as, for example, high and low density polyethylene, polypropylene, ethylene-propylene copolymers, ethylene-vinylacetate copolymers, polybutadiene, polyisoprene, polystyrene, styrene-butadiene copolymers, acrylonitrile-butadiene-styrene copolymers, vinyl- and vinylidene chloride polymers and copolymers, polyoxymethylene, polyethylene-terephthalate, nylon 66, nylon 6, nylon 12, polyurethanes, insaturated polyesters.

The compounds of formula (I) are particularly useful as light stabilizers for polyolefins and more particularly for polyolefin articles of manufacturing having a reduced thickness, such as fibers and films. In a surprising manner said compounds are hardly liable to be extracted from said thin articles, when brought in contact with water or an aqueous surfactant solution.

The compounds of formula (I) can be employed in a mixture with the synthetic polymers in various proportions, depending on the polymer nature, final use and presence of additional additives.

Generally it is preferable to employ from 0.01 to 5% by weight of compounds of formula (I) referred to the polymer weight, more preferably from 0.1 to 1%.

The compounds of formula (I) can be included in a polymeric material composition by various procedures, such as dry mixing in the form of powder, or by a wet process in the form of a solution or slurry. In said operation the synthetic polymer can be employed in the form of powder, granulate, solution, slurry or emulsion.

The polymers stabilized by the products of formula (I) can be used for the manufacture of molded articles, films, tapes, fibers, monofilaments and the like.

A mixture of compounds of formula (I) and synthetic polymers can be optionally additioned with other additives, such as antioxidants, UV absorbers, nickel stabilizers, pigments, charges, plastifying agents, antistatic agents, flame retardants, lubricating agents, anticorrosive agents, metal inhibitors, and the like.

Particular examples of additives which can be employed in a mixture with the polytriazine compounds of formula (I) are:

phenolic antioxidants, such as 2,6-ditert-butyl-p-cresol, 4,4'-thiobis-(3-methyl-6-tertbutylphenol), 1,1,3-tris-(2-methyl-4-hydroxy-5-tertbutylphenyl)butane, octadecyl-3-(3,5-diterbutyl-4-hydroxyphenyl)propionate, pentaerythritol-tetra-(3,5-ditert-butyl-4-hydroxyphenyl)-propionate, tris-(3,5-ditert-butyl-4-hydroxybenzyl)isocyanurate;

esters of thiodipropionic acid, such as di-n-dodecyl-thiodipropionate, di-n-octadecyl-thiodipropionate, aliphatic sulfides and disulfides, such as di-n-dodecyl-sulfide, di-n-octadecyl-sulfide, di-n-octadecyldisulfide;

aliphatic, aromatic or aliphatic-aromatic phosphites and thiophosphites, such as tri-n-dodecyl-phosphite, tris-(n-nonylphenyl)phosphite, tri-n-dodecyl-trithiophosphite, phenyl-di-n-decylphosphite, di-n-octadecyl-pentaerythritoldiphosphite;

UV absorbers such as 2-hydroxy-4-n-octyloxybenzophenone, 2-hydroxy-4-n-dodecyloxybenzophenone, 2-(2'-hydroxy-3',5'-ditert-butylphenyl)-5-chlorobenzotriazole, 2-(2'-hydroxy-3',5'-di-tert-amylphenyl)benzotriazole, 2,4-ditertbutylphenyl-3,5-diterbutyl-4-hydroxybenzoate, phenyl-salicylate, p-tertbutylphenyl-salicylate, 2,2'-dioctyloxy-5,5'-ditertbutyloxanilide, 2-ethoxy-5-tertbutyl-2'-ethyloxanilide;

nickel stabilizers such as Ni monoethyl-3,5-di-tertbutyl-4-hydroxybenzylphosphonate, butylamine-Ni 2,2'-thiobis-(4-tertoctylphenolate) complex, Ni 2,2'-thio-bis-(4-tertoctylphenolphenolate, Ni dibutyldithiocarbamate, Ni 3,5-ditertbutyl 4-hydroxybenzoate, Ni complex of 2-hydroxy-4-n-octyloxybenzophenone;

organo-tin compounds, such as dibutyl-tin-maleate, dibutyl-tin-laurate, di-n-octyl-tin-maleate;

acrylic esters, such as ethyl-α-cyano-β,β-diphenylacrylate, methyl-α-cyano-β-methyl-4-methoxycinnamate;

metal salts of higher fat acids, such as calcium, barium, zinc, cadmium, lead, nickel stearates, calcium cadmium, barium, zinc laurates.

In the following several examples are described, in an illustrative and not limitative way, for illustrating the usefulness of the compounds of formula (I) obtained in examples 1-8, for the stabilization of synthetic polymers.

The results of the tests are listed in Tables 2, 3 and 4 and compared with tests carried out without using any stabilizer and using a known stabilizer commercially available.

EXAMPLE 9

2.5 g of each of the compounds listed in Table 2 below, dissolved in 100 ml chloroform, were mixed with 1000 g polypropylene (Moplen C, manufactured by Societa Montedison, Italy, 1 g n-octadecyl-3(3,5-diterbutyl-4-hydroxyphenyl)propionate and 1 g calcium stearate.

The solvent was removed in an oven under vacuum at a temperature of 50° C for 4 hours.

The dry mixture so obtained was then extruded at a temperature of 200° C and made into granules, wherefrom 0.2 mm thick plates were produced by diecasting at 200° C.

Said plates were exposed in a xenotest 150 apparatus at a black panel temperature of 60° C and the increase in the content of carbonyl groups was periodically determined using the not exposed specimens for balancing the polymer original absorption. The time (T 0.1) required to have a ΔCO% = 0.1 at 5.85 μm was then calculated.

As a comparison, a polymer plate was produced under the same conditions, but without addition of any light stabilizer, and another one with the addition of 2.5 g of 2-hydroxy-4-n-octyloxybenzophenone, a usual commercial stabilizer.

The results are referred in Table 2.

Table 2

| Stabilizer | T 0.1 (hours) |
| --- | --- |
| None | 280 |
| 2-hydroxy-4-n-octyloxybenzophenone | 900 |
| Compound of example 1 | 1320 |
| Compound of example 2 | 1030 |
| Compound of example 3 | 1170 |
| Compound of example 4 | 1240 |
| Compound of example 5 | 980 |
| Compound of example 6 | 1510 |
| Compound of example 7 | 1050 |
| Compound of example 8 | 1180 |

EXAMPLE 10

2 g of each of the compounds listed in Table 3 below, dissolved in 100 ml chloroform, were mixed with 1000 g of high density polyethylene (Moplen RO, manufactured by Societa Montedison, Italy), 0.5 g of n-octadecyl-3(3,5-diterbutyl-4-hydroxy-phenyl)propionate and 1 g of calcium stearate.

The solvent was removed in an oven under vacuum at a temperature of 50° C for 4 hours.

The dry mixture so obtained was then extruded at a temperature of 190° C and made into granules, wherefrom by diecasting plates 0.2 mm thick were produced, said plates were exposed in a Xenotest 150 apparatus, as in example 9.

The time T 0.05 required to have ΔCO% = 0.05 at 5.85 μm was determined.

As a comparison, under the same conditions a polymer plate was produced without addition of any light stabilizer and another plate was produced with addition of 2 g of 2-hydroxy-4-n-octyloxybenzophenone.

The results are referred in Table 3.

Table 3

| Stabilizer | T 0.05 (hours) |
| --- | --- |
| None | 320 |
| 2-hydroxy-4-n-octyloxybenzophenone | 1100 |
| Compound of example 1 | 2030 |
| Compound of example 2 | 1460 |
| Compound of example 3 | 2180 |
| Compound of example 4 | 2070 |
| Compound of example 5 | 1520 |
| Compound of example 6 | 2200 |
| Compound of example 7 | 1710 |
| Compound of example 8 | 1890 |

EXAMPLE 11

The polypropylene granules produced in example 9 were made into fibers under the following conditions:

Extruder temperature: 250°-260° C
Die temperature: 250° C
Stretching ratio: 1:4
Multifilament count: 1020/200 den The fibers were assembled on a white paperboard and exposed until brittleness in Xenotest 150 at a black panel temperature of 60° C.

Another lot of the same fibers were subjected to tests of extraction fastness under the following conditions: the fibers fixed to a stainless steel frame, were soaked into an aqueous solution containing 0.5% b.w. of a commercially available surfactant "DIXAN", under stirring at a temperature of 80° C.

After 10 hours treating, the fibers were rinsed with distilled water, dried and exposed until brittleness to the Xenotest 150 under the same conditions as above.

As a comparison under the same conditions, polypropylene fibers were produced and treated with addition of 0.25% by weight of 2-hydroxy-4-n-octyloxybenzophenone.

The results obtained are referred in Table 4.

Table 4

| Stabilizer | Time to brittleness (hours) | |
| --- | --- | --- |
| | Not Treated fibers | Treated fibers |
| 2-hydroxy-4-n-octyloxybenzophenone | 670 | 360 |
| Compound of example 1 | 1050 | 860 |
| Compound of example 2 | 860 | 750 |
| Compound of example 3 | 1130 | 930 |
| Compound of example 4 | 1170 | 1090 |
| Compound of example 5 | 980 | 810 |
| Compound of example 6 | 1230 | 1110 |
| Compound of example 7 | 920 | 800 |
| Compound of example 8 | 970 | 830 |

From the test results, a considerable increase in the time required to induce a degradation in a polymer stabilized by the invention compounds can be observed with respect to the same polymer not stabilized. Furthermore, clearly improved effects induced by the invention compounds can be observed in comparison with a similar proportion of a prior art additive.

It will further appreciate from Table 4 that the stabilizers of the invention maintain a very high proportion of their activity, when the stabilized fibers have been treated so as to promote the extraction thereof from the polymer, even when the polymer is in the very thin form of a fiber or film.

We claim:

1. A compound having the formula (I):

$$A \left[ -X-R_1-Y-\underset{\underset{\underset{R_2}{|}}{(Z)_m}}{\overset{N=}{\underset{N}{\bigvee}}}\hspace{-6pt}\underset{N}{\overset{N}{\diagdown}} -B \right]_n \quad (I)$$

wherein
X, Y, Z, the same or different, is a member selected from —O—, —S—, $$-\underset{R_3}{\overset{|}{N}}-,$$

$R_3$ being a member selected from hydrogen, straight or branched chain $C_1$ to $C_{18}$ alkyl, $C_5$ to $C_{18}$ cycloalkyl, substituted or not substituted $C_6$ to $C_{18}$ aryl, $C_7$ to $C_{18}$ aralkyl, a piperidine radical of formula (II):

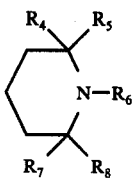
(II)

wherein $R_4$, $R_5$, $R_7$, $R_8$, the same or different, are members selected from $C_1$ to $C_6$ alkyl, and $R_6$ is selected from H, O, $C_1$ to $C_{18}$ straight or branched chain alkyl, $C_2$ to $C_{18}$ alkenyl or alkynyl, $C_7$ to $C_{18}$ aralkyl;

$R_1$ is selected from $C_2$ to $C_{18}$ straight or branched chain alkylene, $C_5$ to $C_{18}$ cycloalkylene, $C_6$ to $C_{18}$ arylene, $C_7$ to $C_{18}$ aralkylene;

$R_2$ is selected from hydrogen, chlorine, bromine, —OH, $C_1$ to $C_{18}$ straight or branched chain alkyl, $C_5$ to $C_{18}$ cycloalkyl, substituted or not substituted $C_6$ to $C_{18}$ aryl, $C_7$ to $C_{18}$ aralkyl, a piperidine radical of formula (II), a group

wherein $R_{11}$, $R_{12}$ are selected from hydrogen or $C_1$ to $C_{12}$ alkyl, $C_5$ to $C_{12}$ cycloalkyl, $C_6$ to $C_{12}$ aryl, $C_7$ to $C_{12}$ aralkyl;

m is an integer from 0 to 1;

n is an integer from 2 to 200;

A, B are the terminal groups, A being H or

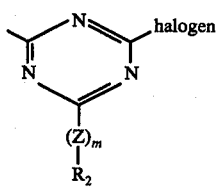

and B is halogen or —X—$R_1$—YH;

or where —X$R_1$—Y— represent a bivalent heterocyclic group having 6 to 8 nitrogen atoms with X and y each representing a disubstituted nitrogen atom; or where —X—$R_1$—Y— represent a residue

in which $R_9$ and $R_{10}$ are hydrogen, $C_1$ to $C_{12}$ alkyl, $C_5$ to $C_{12}$ cycloalkyl, $C_6$ to $C_{12}$ aryl, or $C_7$ to $C_{12}$ aralkyl;

with the proviso that at least one of the radicals —X—$R_1$—Y— and —(Z)$_m$—$R_2$ contains a piperidine radical of formula (II).

2. A compound according to claim 1 having the formula (I):

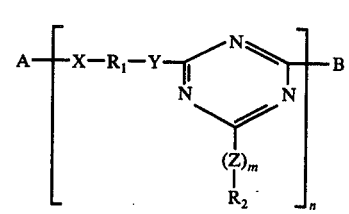
(I)

wherein

X, Y, Z, the same or different, is a member selected from —O—, —S—,

$R_3$ being a member selected from hydrogen, straight or branched chain $C_1$ to $C_{18}$ alkyl, $C_5$ to $C_{18}$ cycloalkyl, substituted or not substituted $C_6$ to $C_{18}$ aryl, $C_7$ to $C_{18}$ aralkyl, a piperidine radical of formula (II):

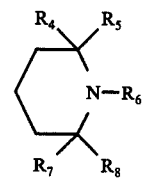
(II)

wherein $R_4$, $R_5$, $R_7$, $R_8$, the same or different, are members selected from $C_1$ to $C_6$ alkyl, and $R_6$ is selected from H, O, $C_1$ to $C_{18}$ straight or branched chain alkyl, $C_2$ to $C_{18}$ alkenyl or alkynyl, $C_7$ to $C_{18}$ aralkyl;

$R_1$ is selected from $C_2$ to $C_{18}$ straight or branched chain alkylene, $C_5$ to $C_{18}$ cycloalkylene, $C_6$ to $C_{18}$ arylene, $C_7$ to $C_{18}$ aralkylene;

$R_2$ is selected from hydrogen, chlorine, bromine, -OH, $C_1$ to $C_{18}$ straight or branched chain alkyl, $C_5$ to $C_{18}$ cycloalkyl, substituted or not substituted $C_6$ to $C_{18}$ aryl, $C_7$ to $C_{18}$ aralkyl, a piperidine radical of form-1a (II), a group

wherein $R_{11}$, $R_{12}$ are selected from hydrogen or $C_1$ to $C_{12}$ alkyl, $C_5$ to $C_{12}$ cycloalkyl, $C_6$ to $C_{12}$ aryl, $C_7$ to $C_{12}$ aralkyl;

m is an integer from 0 to 1;

n is an integer from 2 to 200;

A, B are the terminal groups, A being H or

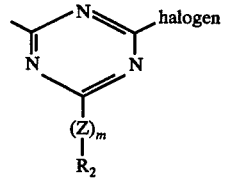

and B is halogen or —X—$R_1$—YH;

in formula (I) the condition there is that at least one of the radicals —X—$R_1$—Y— and —(Z)$_m$—$R_2$ contains a piperidine radical of formula (II).

3. A compound according to claim 2, wherein —X—R$_1$—Y— represents a bivalent radical of a heterocyclic compound having 6 to 8 members, containing 2 nitrogen atoms, X and Y each representing a disubstituted nitrogen atom.

4. A compound according to claim 2, wherein the group —X—R$_1$—Y— represents a residue $$-\underset{\underset{R_9}{|}}{N}-\underset{\underset{R_{10}}{|}}{N}-,$$

in which R$_9$ and R$_{10}$, the same or different are members selected from hydrogen, C$_1$ to C$_{12}$ alkyl, C$_5$ to C$_{12}$ cycloalkyl, C$_6$ to C$_{12}$ aryl, C$_7$ to C$_{12}$ aralkyl.

5. A compound according to claim 2, wherein $m$ is one and the radical R$_2$—Z— is the same as —X—R$_1$—YH.

6. A compound according to claim 2, wherein R$_3$ is selected from hydrogen, C$_1$ to C$_{12}$ straight or branched chain alkyl, and a piperidine radical of formula (II).

7. A compound according to claim 2, wherein R$_1$ is selected from straight or branched chain C$_2$ to C$_{10}$, alkylene, and C$_6$ to C$_{10}$ arylene.

8. A compound according to claim 2, wherein R$_2$ is selected from hydrogen, a C$_1$ to C$_{12}$ straight or branched chain alkyl, and a piperidine radical of formula (II).

9. A compound according to claim 2, wherein the radical R$_2$—Z— is $$-\underset{\underset{Pip}{|}}{N}-(CH_2)_{\overline{2\,to\,6}}-\underset{\underset{Pip}{|}}{N}H,$$

Pip being the radical of formula (II).

10. A compound according to claim 2, wherein A is hydrogen and B is —X—R$_1$—YH.

11. A compound according to claim 9, wherein A is hydrogen and B is $$-\underset{\underset{Pip}{|}}{N}-(CH_2)_{\overline{3\,to\,6}}-\underset{\underset{Pip}{|}}{N}H.$$

12. A compound according to claim 2, wherein R$_4$, R$_5$, R$_7$, R$_8$ are each methyl and R$_6$ is hydrogen or methyl.

13. A compound according to claim 2, wherein
R$_1$ is C$_2$ to C$_{10}$ alkylene or C$_6$ to C$_8$ arylene;
R$_2$ is H, C$_4$ to C$_{12}$ alkyl or piperidyl of formula (II);
R$_3$ is H, C$_4$ to C$_{12}$ alkyl or piperidyl of formula (II);
R$_4$, R$_5$, R$_7$ and R$_8$ are methyl;
R$_6$ is hydrogen or methyl;
R$_9$, R$_{10}$, R$_{11}$, R$_{12}$ are hydrogen;
X, Y, Z represents —O—, —NH—, or $$-\underset{\underset{Pip}{|}}{N}-,$$

Pip being a piperidyl of formula (II);
A is H;
B is $$-\underset{\underset{Pip}{|}}{N}-(CH_2)_r-\underset{\underset{Pip}{|}}{N}H,$$

$r$ being an integer from 2 to 6;

$m$ is 0 or 1; and $n$ is an integer from 2 to 100.

14. A synthetic polymer of increased stability having incorporated with the polymer an amount of a compound according to claim 1 effective to increase the light stability of the polymer.

15. A composition according to claim 14 wherein —XR$_1$—Y— represent a bivalent heterocyclic group having 6 to 8 nitrogen atoms with X and Y each representing a disubstituted nitrogen atom or where —X—R$_1$—Y— represent a residue $$-\underset{\underset{R_9}{|}}{N}-\underset{\underset{R_{10}}{|}}{N}-.$$

16. A composition according to claim 14, wherein said synthetic polymer is a polyolefin.

17. A composition according to claim 16, wherein said synthetic polymer is polypropylene.

18. A composition according to claim 16, wherein said synthetic polymer is polyethylene.

19. A composition according to claim 16, wherein said synthetic polymer is in the form of fibers or film.

20. A composition according to claim 14, wherein said compound is added to the synthetic polymer composition in an amount from 0.1 to 1% by weight referred to the synthetic polymer composition.

21. A synthetic polymer of increased stability having incorporated with the polymer an amount of a compound according to claim 2 effective to increase the light stability of the polymer.

22. A method of producing a compound having the general formula (I):

$$A\leftarrow X-R_1-Y-\underset{\underset{\underset{R_2}{|}}{(Z)_m}}{\underset{|}{\overset{N}{\underset{||}{\underset{N}{\bigcirc}}}}}-B \quad (I)$$

wherein
X, Y, Z, the same or different, is a member selected from —O—, —S—, $$-\underset{\underset{R_3}{|}}{N}-,$$

R$_3$ being a member selected from hydrogen, straight or branched chain C$_1$ to C$_{18}$ alkyl, C$_5$ to C$_{18}$ cycloalkyl, substituted or not substituted C$_6$ to C$_{18}$ aryl, C$_7$ to C$_{18}$ aralkyl, a piperidine radical of formula (II):

(II)

wherein
R$_4$, R$_5$, R$_7$, R$_8$, the same or different, are members selected from C$_1$ to C$_6$ alkyl, and R$_6$ is selected from H, O, $C_1$ to $C_{18}$ straight or branched chain alkyl, $C_2$ to $C_{18}$ alkenyl or alkynyl, $C_7$ to $C_{18}$ aralkyl;

$R_1$ is selected from $C_2$ to $C_{18}$ straight or branched chain alkylene, $C_5$ to $C_{18}$ cycloalkylene, $C_6$ to $C_{18}$ arylene, $C_7$ to $C_{18}$ aralkylene;

$R_2$ is selected from hydrogen, chlorine, bromine, -OH $C_1$ to $C_{18}$ straight or branched chain alkyl, $C_5$ to $C_{18}$ cycloalkyl, substituted or not substituted $C_6$ to $C_{18}$ aryl, $C_7$ to $C_{18}$ aralkyl, a piperidine radical of formula (II), a group

wherein $R_{11}$, $R_{12}$ are selected from hydrogen or $C_1$ to $C_{12}$ alkyl, $C_5$ to $C_{12}$ cycloalkyl, $C_6$ to $C_{12}$ aryl, $C_7$ to $C_{12}$ aralkyl;

$m$ is an integer from 0 to 1;

$n$ is an integer from 2 to 200;

A, B are the terminal groups, A being H or

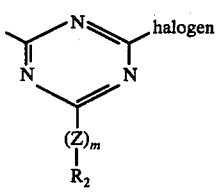

and B is halogen or $-X-R_1-YH$;

in formula (I) there is the condition that at least one of the radicals $-X-R_1-Y-$ and $-(Z)_m-R_2$ contains a piperidine radical of formula (II), comprising reacting a compound of formula (IV):

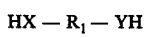

(IV)

X, Y, $R_1$ having the meaning as previously defined, with a member of the group consisting of (a) 2,4-dihalogentriazines of formula (III)

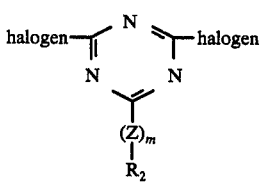

(III)

and (b) cyanuric halide in solution in inert solvent, at a temperature from $-10°$ C to the solvent boiling temperature, in the presence of an organic or inorganic base.

23. The method according to claim 22, comprising reacting 2,4-dihalogentriazines of formula (III) with a compound of formula (IV) in a molar ratio from 1:1.5 to 1.5:1.

24. A method according to claim 22, in which said halogen is chlorine.

25. A method according to claim 22, comprising reacting a cyanuric halide with a compound of formula (IV) in a molar ratio from 1:1 to 1:1.2, to obtain a product having the formula (VI)

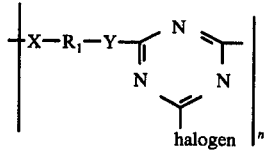

(VI)

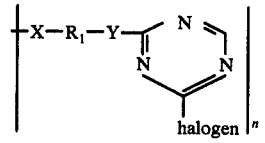

(VI)

in which $m$ is as defined in formula (I) is zero.

26. A method according to claim 25, wherein said product (VI) is successively reacted with a compound of formula (V) to obtain a product of formula (I) in which $m$ is 1.

27. A method according to claim 22, comprising reacting a cyanuric halide with a compound of formula (IV) in a molar ratio from 1:2.4 to 1:2.1 to obtain a product of formula (VII)

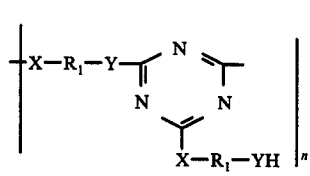

(VII)

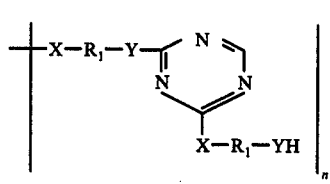

(VII)

28. A method of increasing the light stability of a synthetic polymer, comprising adding to a composition of material of said synthetic polymer, an amount of a compound having the formula (I):

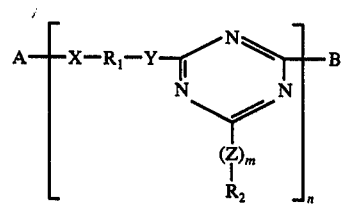

(I)

wherein

X, Y, Z, the same or different, is a member selected from $-O-$, $-S-$,

$R_3$ being a member selected from hydrogen, straight or branched chain $C_1$ to $C_{18}$ alkyl, $C_5$ to $C_{18}$ cycloalkyl, substituted or not substituted $C_6$ to $C_{18}$ aryl, $C_7$ to $C_{18}$ aralkyl, a piperidine radical of formula (II):

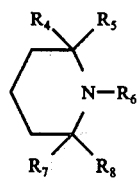 (II)

wherein
$R_4$, $R_5$, $R_7$, $R_8$, the same or different, are members selected from $C_1$ to $C_6$ alkyl, and $R_6$ is selected from H, O, $C_1$ to $C_{18}$ straight or branched chain alkyl, $C_2$ to $C_{18}$ alkenyl or alkynyl, $C_7$ to $C_{18}$ aralkyl;

$R_1$ is selected from $C_2$ to $C_{18}$ straight or branched chain alkylene, $C_5$ to $C_{18}$ cycloalkylene, $C_6$ to $C_{18}$ arylene, $C_7$ to $C_{18}$ aralkylene;

$R_2$ is selected from hydrogen, chlorine, bromine, —OH, $C_1$ to $C_{18}$ straight or branched chain alkyl, $C_5$ to $C_{18}$ cycloalkyl, substituted or not substituted $C_6$ to $C_{18}$ aryl, $C_7$ to $C_{18}$ aralkyl, a piperidine radical of formula (II), a group $$-N-R_{12}$$
$$\phantom{-N-}R_{11}$$

wherein
$R_{11}$, $R_{12}$ are selected from hydrogen or $C_1$ to $C_{12}$ alkyl, $C_5$ to $C_{12}$ cycloalkyl, $C_6$ to $C_{12}$ aryl, $C_7$ to $C_{12}$ aralkyl;
$m$ is an integer from 0 to 1;
$n$ is an integer from 2 to 200;
A, B are the terminal groups, A being H or

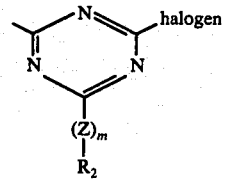

and B is halogen or —X—$R_1$—YH;
in formula (I) ruling the condition that at least one of the radicals —X—$R_1$—Y— and —$(Z)_m$—$R_2$— contains a piperidine radical of formula (II), effective to increase the light stability of said synthetic polymer.

* * * * *